United States Patent
Ciftlik et al.

(10) Patent No.: US 10,634,671 B2
(45) Date of Patent: Apr. 28, 2020

(54) METHODS OF SAMPLE CYCLE MULTIPLEXING AND IN SITU IMAGING

(71) Applicant: LUNAPHORE TECHNOLOGIES SA, Lausanne (CH)

(72) Inventors: Ata Tuna Ciftlik, Morges (CH); Diego Gabriel Dupouy, Preverenges (CH); Pierre Joris, Le Levron (CH); Martin Gijs, Ecublens (CH)

(73) Assignee: LUNAPHORE TECHNOLOGIES SA, Lausanne (CH)

( * ) Notice: Subject to any disclaimer, the term of this patent is extended or adjusted under 35 U.S.C. 154(b) by 3 days.

(21) Appl. No.: 16/076,000

(22) PCT Filed: Feb. 7, 2017

(86) PCT No.: PCT/EP2017/052662
§ 371 (c)(1),
(2) Date: Aug. 7, 2018

(87) PCT Pub. No.: WO2017/137402
PCT Pub. Date: Aug. 17, 2017

(65) Prior Publication Data
US 2019/0346437 A1 Nov. 14, 2019

(30) Foreign Application Priority Data
Feb. 8, 2016 (EP) .................................... 16154746

(51) Int. Cl.
| | | |
|---|---|---|
| *G01N 33/543* | (2006.01) | |
| *C12Q 1/6818* | (2018.01) | |
| *C12Q 1/6832* | (2018.01) | |
| *G01N 33/53* | (2006.01) | |

(52) U.S. Cl.
CPC ..... *G01N 33/54366* (2013.01); *C12Q 1/6818* (2013.01); *C12Q 1/6832* (2013.01); *G01N 33/5306* (2013.01)

(58) Field of Classification Search
CPC .................... G01N 33/54366; C12Q 1/6832
See application file for complete search history.

(56) References Cited

U.S. PATENT DOCUMENTS

| | | | |
|---|---|---|---|
| 2005/0256045 A1 | 11/2005 | Ameri et al. | |
| 2012/0196304 A1* | 8/2012 | Dees ................ | G01N 33/54373 435/7.92 |
| 2014/0055853 A1 | 2/2014 | Corwin et al. | |
| 2015/0005190 A1* | 1/2015 | Ciftlik .................. | B01L 3/5027 506/9 |

FOREIGN PATENT DOCUMENTS

| | | |
|---|---|---|
| EP | 1 131 631 | 1/2009 |
| WO | WO 97/10218 | 3/1997 |
| WO | WO 2007/047450 | 4/2007 |
| WO | WO 2008/005464 | 1/2008 |
| WO | WO 2009/117140 | 9/2009 |
| WO | WO 2010/115089 | 10/2010 |
| WO | WO 2013/058774 | 4/2013 |
| WO | WO 2013/128322 | 9/2013 |
| WO | WO 2014/001935 | 1/2014 |
| WO | WO 2014/035917 | 3/2014 |

OTHER PUBLICATIONS

Kao et al, A fluorescence in situ hybridization (FISH )microfluidic platform for detection of HER2 amplification in cancer cells, 2015, Biosensors and Bioelectronics, 69, 272-279. (Year: 2015).*

Altman, R. B. et al. "Cyanine fluorophore derivatives with enhanced photostability" *Nature Methods*, Jan. 2012, pp. 68-71, vol. 9, No. 1, Online Methods pp. 1-2.

Dodson, K. H. et al. "Retina-on-a-chip: a microfluidic platform for point access signaling studies" *Biomed Microdevices*, 2015, pp. 1-10, vol. 17, No. 114.

Friedenberger, M. et al. "Fluorescence detection of protein clusters in individual cells and tissue sections by using toponome imaging system: sample preparation and measuring procedures" *Nature Protocols*, 2007, pp. 2285-2294, vol. 2, No. 9.

Gerdes, M. J. et al. "Highly multiplexed single-cell analysis of formalin-fixed, paraffin-embedded cancer tissue" *PNAS*, Jul. 16, 2013, pp. 11982-11987, vol. 110, No. 29.

Van Der Velde, J. H. M. et al. "Mechanism of Intramolecular Photostabilization in Self-Healing Cyanine Fluorophores" *ChemPhysChem*, 2013, pp. 4084-4093, vol. 14.

Mathiyarasu, J. et al. "Voltammetric Determination of $_L$-Dopa on Poly(3,4-ethylenedioxythiophene)-Single-Walled Carbon Nanotube Composite Modified Microelectrodes" *Electroanalysis*, 2010, pp. 449-454, vol. 22, No. 4.

Pirici, D. et al. "Antibody Elution Method for Multiple Immunohistochemistry on Primary Antibodies Raised in the Same Species and of the Same Subtype" *Journal of Histochemistry & Cytochemistry*, 2009, pp. 567-575, vol. 57, No. 6.

Schubert, W. etal. "Analyzing proteome topology and function by automated multidimensional fluorescence microscopy" *Nature Biotechnology*, Oct. 1, 2006, pp. 1-9.

Wählby, C. et al. "Sequential Immunofluorescence Staining and Image Analysis for Detection of Large Numbers of Antigens in Individual Cell Nuclei" *Cytometry*, 2002, pp. 32-41, vol. 47.

Xing, Y. et al. "Bioconjugated quantum dots for multiplexed and quantitative immunohistochemistry" *Nature Protocols*, 2007, pp. 1152-1165, vol. 2, No. 5.

(Continued)

*Primary Examiner* — Narayan K Bhat
(74) *Attorney, Agent, or Firm* — Saliwanchik, Lloyd & Eisenschenk

(57) ABSTRACT

The invention relates to a method for in situ imaging of samples by cycle multiplexing that enables imaging of various molecular targets through multi-molecular read-outs on the same sample in a rapid, highly sensitive and reliable manner. The invention is further related to imaging buffers preventing the degradation of the sample and of the imaging reagents, which are particularly useful in a method of in situ imaging of samples by cycle multiplexing according to the invention.

12 Claims, 4 Drawing Sheets

(56) References Cited

OTHER PUBLICATIONS

Zhang, H. et al. "Genotyping by Alkaline Dehybridization Using Graphically Encoded Particles" *Chemistry*, Mar. 1, 2011, pp. 1-15, vol. 17, No. 10.
Written Opinion in International Application No. PCT/EP2017/052662, dated Mar. 20, 2017, pp. 1-6.

* cited by examiner

A

B

METHODS OF SAMPLE CYCLE MULTIPLEXING AND IN SITU IMAGING

CROSS-REFERENCE TO RELATED APPLICATION

This application is the U.S. national stage application of International Patent Application No. PCT/EP2017/052662, filed Feb. 7, 2017.

FIELD OF THE INVENTION

The present invention pertains generally to the fields of in situ imaging of samples, in particular biological samples by cycle multiplexing.

BACKGROUND OF THE INVENTION

Image-based sample analytical measurement techniques have been limited by the number of molecular measurements that can be observed simultaneously (the extent of multiplexing) in a single sample, for example a tissue specimen. This has, so far, constrained this type of analytical approaches from large-scale '-omics' use when compared to other highly multiplexed technologies, such as single-cell sequencing or mass cytometry. As a consequence, essential spatial details, which currently only image-based approaches can reveal, are being missed. Using immunofluorescence rather than classical immunohistochemistry can partly overcome this issue, but measurements are still limited to a maximum of 4-5 simultaneous molecular readouts. The major limitation of image-based multiplexed sample analytical measurements is the separation of distinct signals in a single specimen without cross talk between signals. In case of fluorescence imaging, for example, overlap of spectra prevents a clear separation of the emitted signals in a highly multiplexed multicolor labeling experiment. In addition, fluorophores may exhibit self-quenching behavior at high labeling densities, further limiting the simultaneous application of multiple labels. Another constraint on the multiplexing ability of immuno-based approaches is the requirement that each primary antibody has to be derived from different animal species to ensure specific amplification and detection with secondary antibodies. This could in principle be overcome by direct immunofluorescence, in other words labelling primary antibodies directly, but this approach gives rise to other problems, such as a decreased specificity and a lower signal output due to a lack of amplification.

Multiple molecular readouts using immunofluorescence have been achieved using an antibody mixing method shown in WO 2007/047450. While this method has the advantages of being image-based, applicable to tissue sections and able to be utilized in environments containing non-specific nucleases, the maximum number of simultaneous detections is limited. The inclusion of quantifiable reference standards into the measurement process such as described in WO 2008/005464, while increasing the precision in quantification immunohistochemistry read-outs in certain applications such as semi-quantitative scoring of biomarker proteins, e.g. as applied to semi-quantitative scoring of Human Epidermal Growth Factor 2 (HER2) expression in breast cancer tissues, may further limit the possibility of multiple simultaneous readouts because of dividing the output signals into specific bands.

Sample multiplexing with in situ imaging can be achieved by carrying out spectral multiplexing which comprises applying different stains on the same sample and extracting individual stain images from the imaging results as described in EP 1131631. The technique involves collecting spectral data from each pixel of the sample, computationally generating a spectrum that would have resulted from each individual staining and showing the individual results in a corrected colour spectrum. While allowing for multiple marker quantification, the device performance is inversely proportional to the number of parallel stains because of possible crosstalk between each signal.

Recent advances in immunostaining technologies are highly promising with regard to overcoming the above-mentioned limitations. These technologies make use of multi-cycle in situ imaging, which involves dye-inactivation and/or antibody elution after a usual staining/imaging step to enable additional rounds of staining and imaging.

Those approaches include chemical inactivation of fluorescent dyes after each image acquisition (Gerdes et al., 2013, *PNAS*, 110(29), 11982-11987), non-destructive dissociation of the antibody-antigen bonds for successive staining cycles by sequentially using a tailor-made acidified peimanganate solution (WO 2010/115089), successive antibody elution with various different buffers (Pirici et al., 2009, *J. Histochem. Cytochem.*, 57(6), 567-575), successive cycles of peptide probe contact and denaturation at high temperature for sequential multi-target detection (WO 2009/117140), iterative staining and imaging cycles using a combination of denaturation and elution techniques (Wahlby et al., 2002, *Cytometry*, 47(1), 32-41), multiple sequential staining cycles using bleaching before each restaining step (Friedenberger, 2007, *Nature Protocols*, 2, 2285-2294), use of bioconjugated quantum dots as biological labels for multiplexed profiling of molecular biomarkers (Schubert et. al., 2006, *Nature Biotechnology* 24, 1270-1278), use of water soluble polymers forming bonds with multiple target molecules of interest (Xing, 2007, *Nature Protocols* 2, 1152 1165).

All those multi-cycle in situ imaging approaches are iterative and present the advantages of allowing subsequent utilization of primary antibodies raised in the same species as well as the same chemical reagent or fluorophore for different molecular targets and to theoretically enable identifying an unlimited number of different targets on the same tissue section.

Although promising, translation of multi-cycle in situ imaging technologies to high-throughput, multiplexed molecular profiling of samples such as for example tumour sections is not straightforward. First, long incubation and washing cycles (usually up to several hours) result in extremely long total protocol durations that cause degradation of tissue antigens under fluctuating ambient conditions. Second, repeated mounting/demounting of imaging of sample coverslips steps further deteriorate tissue integrity. Therefore, such manual handling of cycles affects reproducibility and practically impedes reliable molecular profiling of tissue specimens at high-throughput and renders the use of multi-cycle technologies impractical in applications like diagnostic purposes which require high throughput, reliability and relative low-cost implementation characteristics.

A further limitation of the existing methods available for in situ imaging of samples also originates from large-area imaging requirement for realizing multi-cycle assays. Since the specimens are removed from imaging systems to realize manual processing in between each cycle and following the manual processing, the specimens are restored back to imaging systems for a large-area imaging subsequent molecular marker and the images obtained from the specimen at all cycles are overlaid, subtle differences of specimen positioning on the imaging systems at each cycle introduce errors on localization of molecular signals throughout the specimen. This hinders the true localization of molecular signals, in particular those of subcellular features that can only be observed with a high resolution or super-resolution microscopy systems.

Vertical microfluidic systems have also been introduced as a possible tool to be used in immunoassays or genetic analysis. A microfluidic probe which is made up of a wide chamber and vertical access holes has been developed to stain small-area spots on a sample (WO 2014/001935). The dimensions of the stained area in each cycle are at the order of 100 µm. So, it is necessary to scan the sample surface with a number of staining steps to obtain a larger image. The issues of possible localization errors and analysis time increase resulting from the scanning process are also present in this method.

An open-top microfluidic device to facilitate easier transition between sequential staining and imaging steps has been recently presented (WO 2014/035917). The method aims to overcome the several disadvantages of having to de-coverslip the sample between each successive run such as extra time consumption, tissue loss and slide-to-slide image variation by eliminating the need for this step, while it does not address the imaging area and process time requirements.

Finally, it has been observed that in situ imaging involving sequential and repeated fluorophore exposure of the sample leads to induced damages on the sample. In particular, fluorescently labelled antibodies usually get cross-linked to the sample or tissue during imaging and cannot be removed from sample or tissue afterwards, which further limits the use of in situ imaging by cycle multiplexing.

Therefore, there is a need for new techniques, instrumentation and tools for in situ imaging of samples by cycle multiplexing which would allow multi-molecular read-outs on the same sample with high-throughput, high sensitivity, reliability and precision regarding the true localization of the molecular signals, notably for applications in the fields of diagnostics or treatment course monitoring in which the demand is currently considerably expanding.

SUMMARY OF THE INVENTION

An object of this invention is to provide a method for in situ imaging of samples by cycle multiplexing that enables imaging of various molecular targets through multi-molecular read-outs on the same sample in an efficient, accurate and reliable manner.

It is advantageous to provide a method for in situ imaging of samples by cycle multiplexing that enables imaging of various molecular targets on the same sample in a rapid and sensitive manner.

It is advantageous to provide a method of in situ imaging of samples by cycle multiplexing where the sample integrity is maintained by the avoidance of de-mounting the sample from the sample support between each cycle of the multiplexing process.

It is advantageous to provide a method of in situ imaging of samples by cycle multiplexing where the total analysis time is decreased by the avoidance of the need of de-mounting the sample from the sample support between each cycle of the multiplexing process and by preventing the degradation of reproducibility resulting from the de-mounting.

It is advantageous to provide a method of in situ imaging of samples by cycle multiplexing where the sample immobilized on a sample support within a microfluidic channel is subjected to a fully controllable flow of imaging probe(s) directly at the surface of the sample flowed directly at the surface of the sample in a specific sequence for carrying out a complete cycle of sample labelling and imaging and repeating such cycle in a high-throughput manner.

It is advantageous to provide a method of in situ imaging of samples by cycle multiplexing where the sample integrity is preserved during the imaging cycles through the use of imaging buffers preventing the degradation of the sample and the degradation of the imaging probe(s) through the formation of free radical oxygen species during the multiplexing process.

It is advantageous to provide an imaging buffer preventing the cross-linking of imaging reagents under high intensity fluorescent light which, when used in a method of in situ imaging by cycle multiplexing according to the invention decreases the reagent elution time necessary at each subsequent cycle and increases the number of possible sample labeling cycles without degradation of reproducibility and/or sensitivity of the measured imaging signal.

Objects of this invention have been achieved by providing a method according to claim 1.

Disclosed herein, according to a first aspect of the invention, is a method for in situ imaging of samples by cycle multiplexing comprising the steps of:
  (i) providing a sample immobilized on a sample support;
  (ii) providing a microfluidic device comprising a microfluidic chamber, at least one fluid inlet at one end of said microfluidic chamber and at least one fluid outlet at another end of said microfluidic chamber configured to conduct a fluid supplied from a fluid feeding system under pressure through the microfluidic chamber for advective transport of fluidic substances and reagents inside said microfluidic chamber in a uniform manner, wherein at least one wall of the microfluidic chamber is formed by the sample support and wherein the volume of the microfluidic chamber is from about 2.5 µl and 200 µl;
  (iii) mounting said sample support over said microfluidic chamber with the sample facing the inside of the microfluidic chamber;
  (iv) injecting in sequence a plurality of reagents, including at least one imaging probe, through the fluid inlet into the microfluidic chamber, at a flow rate in a range between about 1 µl/s and about 100 µl/s;
  (v) imaging a signal emitted by components of the sample reacted with said at least one imaging probe;
  (vi) repeating steps (iv) and (v) with different imaging probes;
wherein said injecting in sequence a plurality of reagents includes:
  an elution step where an elution buffer is injected for removing undesirable material such as labelling probes (e.g. antibodies or markers) potentially remaining on the sample;
  a non-specific binding blocking step where a blocking buffer is injected;
  a sample labelling step where an imaging probe is injected; and
  an optional pre-imaging step where an imaging buffer is injected, wherein each of these steps may be preceded and/or followed by an optional washing step wherein a washing buffer is injected.

DETAILED DESCRIPTION OF THE INVENTION

Figure 1:
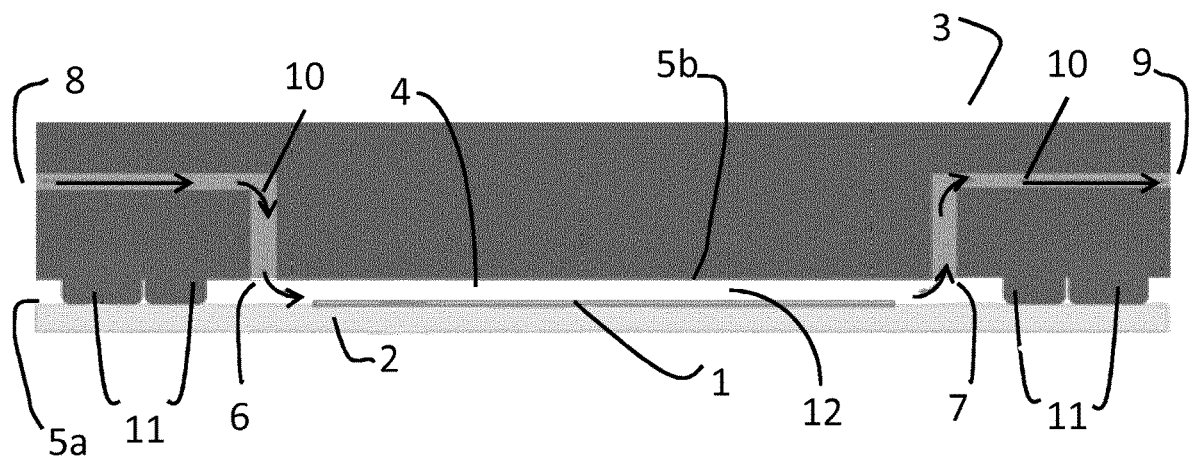
FIG. 1 is an illustration of exemplary settings for a device carrying out the process of the invention as described in Example 1.

Referring to the figures, in particular first to FIGS. 1 and 2, is provided an illustration of a method for in situ imaging of samples by cycle multiplexing comprising the steps of:
(i) providing a sample (1) immobilized on a sample support (2);
(ii) providing a microfluidic device (3) comprising a microfluidic chamber (4), at
least one fluid inlet (6) at one end of said microfluidic chamber and at least one fluid outlet (7) at another end of said microfluidic chamber configured to conduct a fluid supplied from a fluid feeding system under pressure (8) through the microfluidic chamber for advective transport of fluidic substances and reagents inside (10) said microfluidic chamber in a uniform manner, wherein at least one wall of the microfluidic chamber (5a) is formed by the sample support (2) and is mounted in a removable manner to the other wall of the microfluidic chamber (5b) through holding means (11) and wherein the volume of the microfluidic chamber is from about 2.5 μL and 200 μl;
(iii) mounting said sample support over said microfluidic chamber with the sample (1) facing the inside of the microfluidic chamber (12);
(iv) injecting in sequence a plurality of reagents, including at least one imaging probe, through the fluid inlet (6) into the microfluidic chamber, at a flow rate in a range between about 1 μl/s and about 100 μl/s;
(v) imaging a signal emitted by components of the sample reacted with said at least one imaging probe;
(vi) repeating steps (iv) and (v) with different imaging probes;
wherein said injecting in sequence a plurality of reagents includes:
an optional elution step (S1) where an elution buffer is injected for removing undesirable material such as labelling probes (e.g. antibodies or markers) potentially remaining on the sample;
a non-specific binding blocking step (S2) where a blocking buffer is injected;
a sample labelling step where an imaging probe is injected (S3 comprising S3' and S3'''); and
a pre-imaging step (S4) where an imaging buffer is injected, wherein each of these steps may be preceded and/or followed by an optional washing step wherein a washing buffer is injected.

In another embodiment, the imaging probe is a labelled probe suitable for interacting with specific molecular entities on the sample. For example, an imaging probe can be a labeled RNA or DNA sequence useful for hybridizing in-situ with RNA or DNA sequences from the sample (complementary sequences). In another example, the imaging probe is a labeled primary antibody (e.g. fluorescent), which binds directly the target antigen.

In another embodiment, the imaging probe results from the injection of a sequence of labelling probes such as specific antibodies and chromogen or fluorescent detection molecules, targeting the molecular entities to be analyzed within the sample. In one embodiment, the imaging probe results from a labeled secondary (e.g. fluorescent) antibody that is injected after a primary antibody.

According to a particular embodiment, the flow rate of the injected plurality of reagents is a range from about 1 μl/s to about 30 μl/s, such as from about 5 μl/s to about 30 μl/s (e.g. about 25 μl/s).

According to another particular embodiment, the height of the microfluidic chamber as defined by the distance from the sample support wall to opposite wall of the microfluidic chamber ranges from about 10 μm and about 300 μm, and the diagonal or the diameter of the microfluidic chamber ranges from about 100 μm and about 56 mm, forming a shallow and wide geometry.

In another embodiment, each step in the sequence of injected plurality of reagents is applied for a period of time necessary to flush out the previous solution in the solution flow step sequence from the microfluidic chamber, wherein the flush out corresponds to a concentration decrease of the previous solution down to 1% of the previously injected concentration.

In another embodiment, each step in the sequence of injected plurality of reagents is applied for a period of time necessary to increase the concentration of the injected solution up to 99% of the intended protocol concentration within the microfluidic chamber.

In an embodiment, each step in the sequence of injected plurality of reagents lasts from about 1 s to about 120 s, such as from about 5 s to about 20 s (e.g. about 10 s).

In another particular embodiment, the step of injecting in sequence a plurality of reagents includes:
a washing step wherein a washing buffer is injected (S0);
a non-specific binding blocking step (S2) where a blocking buffer is injected;
an optional incubation step, where the previously injected blocking buffer is incubated with or without any flow condition;
an optional washing step, where a washing buffer is injected;
a sample labeling step where a imaging an imaging probe is injected (S3);
an optional incubation step, where the previously injected imaging probe is incubated with or without any flow condition;
a washing step wherein a washing buffer is injected (S3a);
an optional pre-imaging step (S4) where an imaging buffer is injected;

wherein the sample labeling step comprises injecting either directly a labeled probe or a sequence of labelling probes leading to an imaging probe.

According to a particular embodiment, the sample labeling step comprises injecting a sequence of labelling probes leading to an imaging probe which comprises a first step wherein a primary antibody is injected (S3'), a washing step wherein a washing buffer is injected (S3") and a further step wherein a labeled secondary antibody is injected (S3'").

In a particular embodiment, the sample labeling step comprises a first step wherein a primary antibody is injected (SB3'), a washing step wherein a washing buffer is injected (SB3"), a second step wherein an enzyme-linked secondary antibody is injected (SB3'"), a washing step wherein a washing buffer is injected (SB3""), and a further step where a chromogen or a fluorescent detection molecule reacting with the enzyme that is linked to the secondary antibody is injected SB3""'.

In another particular embodiment, the sample labeling step comprises a first step wherein a primary antibody is injected (SB3'), a washing step wherein a washing buffer is injected (SC3"), a second step where a post-primary antibody is injected, a washing step wherein a washing buffer is injected (SC3"), a third step wherein an enzyme linked secondary antibody is injected (SC3'"), a washing step wherein a washing buffer is injected (SC3""), and a further step where a chromogen or a fluorescent detection molecule reacting with the enzyme that is linked to secondary antibody is injected SC3""'.

In another particular embodiment, the sample labeling step comprises injecting at least one labeled probe such for in-situ hybridization with some DNA/RNA material within the sample, such as a labeled RNA or DNA probe.

In a further particular embodiment, when the sample labeling step comprises injecting at least one labeled probe such for in-situ hybridization with some DNA/RNA material within the sample, the method of the invention further comprises applying temperature cycles within the microfluidic chamber required for hybridization and de-hybridization step of some DNA/RNA material within the sample with the RNA or DNA probes (complementary sequences). For example, heaters external to the microfluidic chamber or sample support can apply such temperature cycles. In-situ hybridization can be achieved for example as defined in *Modern Pathology*, 2011, 24, 613-623; doi:10.1038/modpathol.2010.228). Imaging is then achieved on the immobilized hybridization probes for RNA and DNA sequence detection (labelled complementary sequence probes).

In a particular embodiment, when the sample labeling step comprises injecting at least one labeled probe such for in-situ hybridization with some DNA/RNA material within the sample, the injection of the labeled probe is followed by an injection of an imaging buffer, in particular for example an imaging buffer comprising at least one anti-oxidant and/or radical scavenger as described herein.

In another particular embodiment, when the sample labeling step comprises injecting at least one labeled probe such for in-situ hybridization with some DNA/RNA material within the sample is used, an elution step is carried out while applying a temperature cycle (e.g. at a temperature range from about 10° C. and about 100° C.) for ensuring removal of undesirable in-situ hybridized probes or markers potentially remaining on the sample before repeating the method with another sample labelling step. In this case, the elution buffer may comprise an alkaline dehybridization buffer as described in Zhang et al., 2011, 17(10): 2867-2873 (e.g. at pH 11.2) and the elution step is followed by a washing step with a washing buffer at a dehybridization temperature (e.g. at a temperature range from about 10° C. and about 100° C.) before carrying out a new sample labelling step.

In a particular embodiment, each step in the sequence of injected plurality of reagents comprises for each reagent two flow rate steps:
  a first flow rate step where the reagent is injected at an initial flow rate in a range between about 1 µl/s and about 100 µl/s;
  a second flow rate step where the same reagent is injected at a lower flow (typically from about 0.001 to about 1.0 µl/s) to ensure sufficient flux of the said reagent with the sample, before injecting the next reagent in the sequence.

In a further particular embodiment, the second flow rate step of a reagent lasts from about 1 min to about 30 min (e.g. from about 2 to about 15 min).

According to a particular embodiment, the duration of the second flow rate step depends on the volume the microfluidic channel used and the time necessary to the incubation of the reagent with the sample. A calculated incubation time of around 1 minute is required for a chamber height less than 100 µm.

In an embodiment, the imaging step (v) is conducted by confocal fluorescence microscopy.

In an embodiment, the imaging step (v) is conducted by fluorescence microscopy.

In an embodiment, the imaging step (v) is conducted by bright-field microscopy.

According to a particular embodiment, a washing buffer is selected from a Phosphate Buffered Saline (PBS) and Tris-buffered Saline (TBS).

According to a particular embodiment, an elution buffer is selected from a solution with a low pH (e.g. pH 2) supplemented with a detergent (TritonX). The elution buffer solution may further contain high ionic salt concentrations (for example from about 0.001 M NaCl up to about 1 M NaCl), chaotropic agents, and/or reducing/oxidizing agents.

According to a particular embodiment, a blocking buffer is selected from sodium citrate buffer and PBS supplemented with protein (e.g. Bovine Serum Albumin or serum) and/or detergent (e.g. Tween).

According to a particular embodiment, the non-specific binding blocking step (S2) is optional.

According to a particular embodiment, the sample labeling step comprises a first step wherein a primary antibody is injected (S3'), a washing step wherein a washing buffer is injected (S3") and a further step wherein a secondary antibody is injected (S3'").

According to a particular embodiment, the primary antibodies of the invention may be any suitable antibodies for any immunohistochemistry and immunofluorescent assays such as described in *Dabbs, Diagnostic Immunohistochemistry: theranostic and diagnostic applications*, $4^{th}$ edition, 2014, ISBN 978-1-4557-4461-9. For example, suitable antibodies are mouse or rabbit anti-human Immunoglobulin G or Y antibodies directed against clinically relevant epitopes.

According to another particular embodiment, the imaging buffer comprises at least one anti-oxidant and/or radical scavenger. Examples of anti-oxidant and/or radical scavenger are selected from ascorbic acid, 6-hydroxy-2,5,7,8-tetramethylchroman-2-carboxylic acid (Trolox), cyclooctatetraene, lipoic acid and 4-nitrobenzyl alcohol.

According to another particular embodiment, the imaging buffer is selected from distilled water, Phosphate Buffered Saline (PBS) and Tris-buffered Saline (TBS).

According to another particular embodiment, the imaging buffer according to the invention comprises at least one anti-oxidant and/or radical scavenger, wherein said at least one anti-oxidant and/or radical scavenger are in soluble form i.e. in form of an imaging buffer solution (Altman et al., 2011, *Nat Methods*, 9(1), 68-71).

In another embodiment, the flow is applied in a continuous manner.

According to a particular embodiment, a method according to the invention comprises at least about 2 to 80 cycles of steps (iv) to (vi), in particular at least about 20 to 80 cycles of steps (iv) to (vi).

According to a particular embodiment, a method according to the invention comprises from 2 to up to about 200 cycles of steps (iv) to (vi), in particular from 2 to up to about 20 cycles or from 2 up to about 100 cycles.

Disclosed herein, according to another aspect of the invention, is an imaging buffer comprising at least one anti-oxidant and/or radical scavenger, in particular where said at least one anti-oxidant and/or radical scavenger is at a concentration comprised between about 1 mM and about 1'000 mM (e.g. from about 10 to about 1'000 mM or from about 1 to about 10 mM).

According to a further embodiment, is provided an imaging buffer according to the invention comprising about 10 to about 1'000 mM of ascorbic acid (e.g. about 100 mM) or about 1 to about 10 mM Trolox or lipoic acid.

In a further particular embodiment, is provided a method for in situ imaging of samples by cycle multiplexing as described herein wherein an imaging buffer according to the invention is injected in the pre-imaging step.

According to one aspect, the method of the invention allows in-situ imaging of samples by cycle multiplexing of molecular profiling on various samples, in particular biological samples, including tissue sections, cells cultures, protein or nucleic acid preparations.

According to another aspect, the samples that are provided for analysis by a method of the invention as immobilized by different types of techniques and include formalin-fixed paraffin-embedded (FFPE) tissue samples, cryogenically fixed tissue samples, cell smears, needle biopsy samples and fixed cell preparations. Different types of sample preparation steps can be realized depending on the sample type and desired application.

According to another aspect, the labelling probes comprise chemical dyes, antibodies and antibody fragments, or oligonucleotides leading to an imaging probe such as in situ hybridization or amplification probes.

The above mentioned features may be combined in any appropriate manner.

An advantageous characteristic of the invention is to provide a method where incubation, washing and elution cycle times are decreased to minutes, preventing the degradation of sample antigens under fluctuating ambient conditions and during exposure to harsh buffers.

An advantageous characteristic of the invention is to provide a method allowing carrying out conventional sample labelling such as conventional primary and secondary antibodies combined with conventional detection systems, without necessitating dedicated or tailored reagents, buffers or detection systems for multiple labelling.

A noticeable advantage for a method of the invention is to remove the need to repeatedly mount and demount sample coverslips through each imaging cycle, which may affect sample integrity and result in the degradation of reproducibility and prevent the full automation of such a process, which is also essential for a reproducible labelling.

A further noticeable advantage for a method of the invention is to use 100% of a sample area for multiplexing analysis.

Another advantageous characteristic of the invention is to provide a method which multi-cycle performance can be further improved by using specific imaging buffer compositions during the imaging step to efficiently remove labelling probes such as fluorescent molecules from the analyte during the elution step before carrying out the next analytical step and to prevent photo-induced alterations of the sample or of the labeled molecules used during the sample labelling step.

Apart from sample analysis, a method according to the invention can be useful for multiplexing genetic sequence detection such as by in-situ hybridization.

Other features and advantages of the invention will be apparent from the claims, detailed description, and figures. The invention having been described, the following examples are presented by way of illustration, and not limitation.

EXAMPLES

Example 1: Example of Multiplexing Protocol to Carry Out Successive Sample Labelling Cycles A method of the invention for in situ imaging of samples by cycle multiplexing is implemented in a device on a formalin-fixed paraffin-embedded (FFPE) tissue sample as illustrated on FIG. 1.

a) Example of Sample Preparation

Different types of sample preparation steps can be realized depending on the sample type and desired application. In the present example, the sample preparation steps for FFPE tissue samples which were carried out before multi-staining processes is described here as a typical example.

The biological samples are first dehydrated at 65° C. for 10 min. After 5 minutes of cool-down, the tissue sections are dewaxed for 10 minutes in a Histoclear solution (e.g. Xylol), followed by rehydration in 100%, 95%, 70% and 40% (vol./vol.) ethanol, respectively. Finally, the heat-induced antigen-retrieval process is carried out with a sodium citrate buffer (about pH 6) or EDTA buffer (about pH 9) in a water bath at 95° C. or electric pressure cooker for about 20 minutes. The exact protocol depends on the used labelling probes. The sample is then ready for conducting a method of the invention as illustrated in the following exemplary device.

b) Example of Device for Implementing the Method of the Invention

FIG. 1 shows the cross section of an exemplary device (3) for implementing a method of the invention where a sample (1), for example as prepared under a), is immobilized on a sample support (2) wherein said sample support is maintained on the wall of the microfluidic chamber (5*b*) facing the fluid feed inlet of said microfluidic chamber, such that the sample (1) is facing the inner part of the microfluidic chamber.

c) Example of Imaging Reagent Sequence

The initial cycle of the multiplexing method of the invention can be started after tissue and reagent preparation. An imaging reagent sequence (comprising washing/elution solutions, blocking solutions, labelling probe solutions, etc.) used in a multiplexing method according to the invention utilized to carry out successive sample labelling and imaging cycles is outlined in FIG. 2A. Such an imaging reagent sequence is successively introduced in the microfluidic chamber (4) through the fluid inlet (6) by the fluid feeding system (8).

Step 0: Washing Step

Each cycle starts with first washing the tissue sample by flowing a buffer through the system such as Phosphate Buffered Saline (PBS) and Tris-buffered Saline (TBS).

Step 1: Elution Step

The washing buffer is followed in the sequence of the imaging reagents by an elution buffer, the composition of which and pH conditions can vary depending on the analyzed sample for removing undesirable material (e.g. labelling probes such as antibodies or markers) potentially remaining on the sample. For example, 0.1M glycine buffer at pH 2 supplemented with 0.05% TritonX detergent can be used as elution buffer.

Step 2: Non-Specific Binding Blocking Step

A blocking buffer (e.g. Sodium citrate buffer or PBS-Tween with Bovine Serum Albumin) is then flown in the sequence of the imaging reagent sequence through the microfluidic chamber to lower non-specific binding of proteins in the subsequent steps.

Step 3 (3', 3" & 3'''): Sample Labelling Step(s)

The imaging probe (s) or the labelling probe(s) leading to the imaging probe are then introduced in the sequence of the imaging reagents flown in the microfluidic channel. For example, a sequence of labelling probes leading to a labelled probe includes a sequence where a primary and then a secondary antibody (labelling probes) are flown through and incubated, while washing the sample with a washing buffer between each step. The dilution ratios of labelling probes are determined depending on optimized protocol or vendor instructions.

Alternatively, another example of sample labelling step includes injecting a RNA or DNA labelled probe for in-situ hybridization. In this case, the method further includes applying a suitable temperature cycle for ensuring the hybridization of the RNA or DNA material within the sample with the complementary sequences of the RNA or DNA labelled probes.

Step 4: Imaging Step

Imaging is performed after the end of this cycle and eventually after an imaging buffer has been flown in the microfluidic channel.

The entire cyclic process can be repeated for up to about 50 times with different imaging probes. In case of one cycle where sample labelling is achieved in view of in-situ hybridization, the method may further include applying a temperature cycle for ensuring the removal of undesirable in-situ hybridized probes or markers potentially remaining on the sample before repeating the method with another sample labelling step, e.g. during the elution step.

Figure 2A:
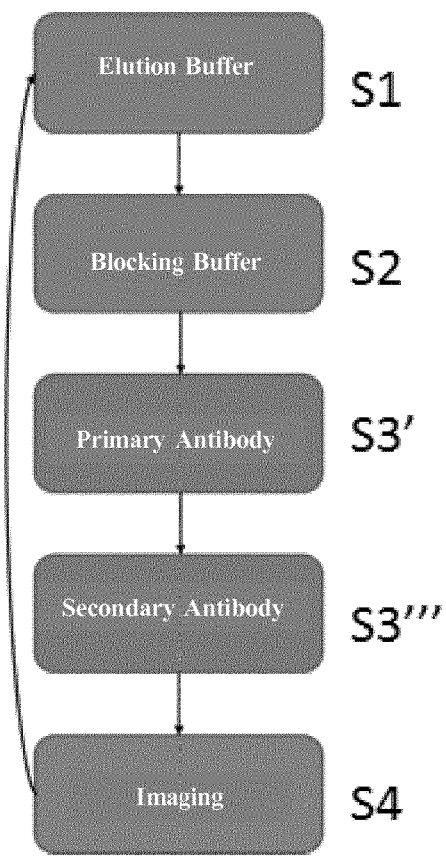
FIG. 2 illustrates a reagent sequence used in the imaging cycle of the method (2A), while omitting the optional washing buffer steps between each major flow steps (S1 to S4) and a flow diagram of multi-sample labeling and imaging process using antibodies targeting various target components (T1, T2, Tn) on a sample as labelling probes showing the sequence of injected reagents and the repeats of the sequence, n times with different reagents (2B).
Figure 2B:
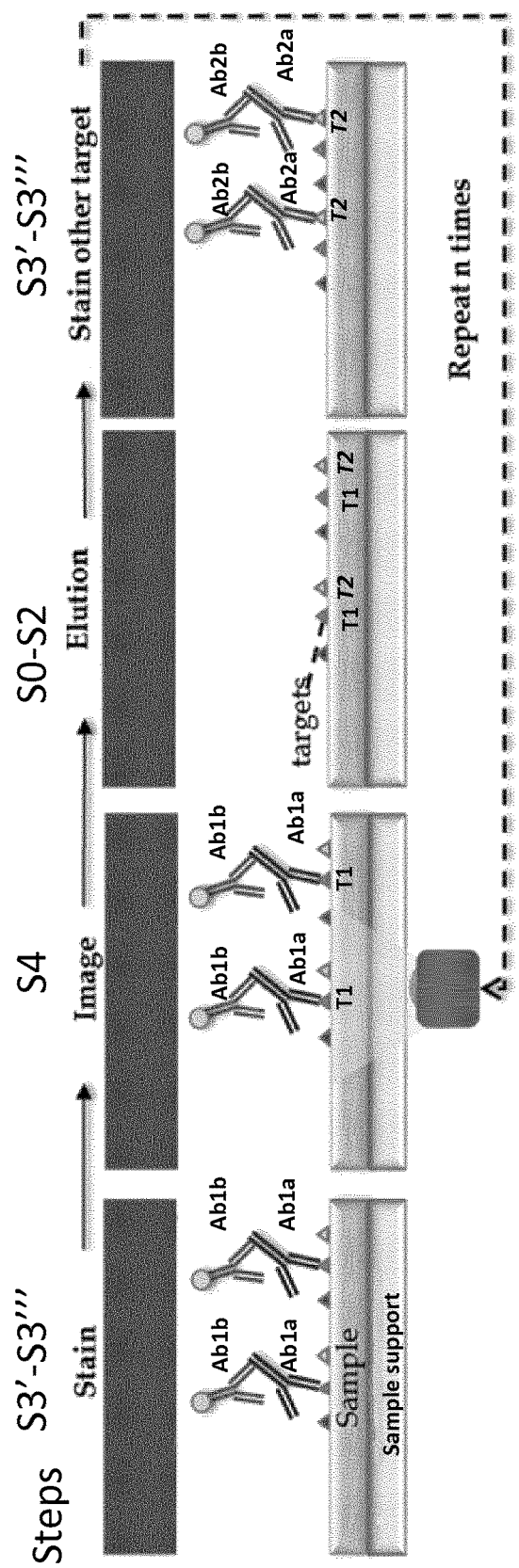

FIG. 2B shows an example of flow diagram of multi-sample labelling and imaging process with primary (a) and then secondary (b) antibodies as labelling probes targeting various targets (T1, T2, Tn) on a sample showing the sequence repetition of the different steps of the imaging reagent sequence outlined in FIG. 2A and the repetition of the sequence n times.

Table 1 below shows an example timing chart of one cycle of sample labelling for a typical application. Each cycle can be reduced down to about less than 10 minutes, thereby leading to a sample labelling time of approximately 5 hours needed to perform about 50 cycles of sample labelling in this particular case. The time of imaging depends on the number of fluorescent channels, imaging area and the required resolution for each cycle, and varies from 1 minute to 120 minutes per step. Therefore, the total time required for imaging and sample labelling can be as low as about 6 hours to complete 50 cycles of sample labelling together with imaging.

TABLE 1

| | Reagent | Flow duration (s) | Incubation time (s) | Step time (s) |
|---|---|---|---|---|
| Cycle (n) | Elution buffer | 12 | 60 | 72 |
| | Washing buffer | 20 | — | 20 |
| | Blocking buffer | 12 | 60 | 72 |
| | Washing buffer | 20 | — | 20 |
| | Primary Ab (n) | 12 | 120 | 132 |
| | Washing buffer | 20 | — | 20 |
| | Secondary Ab (n) | 12 | 120 | 132 |
| | Washing Buffer | 20 | — | 20 |
| | Imaging Buffer | 20 | — | 20 |
| | Total | 148 | 360 | 508 | d) Example of Sample Measurement

Imaging results of successive sample labeling cycles carried out with a method of the invention are as described below.

Cell Culture

HeLa Kyoto cells are cultivated in DMEM (Dulbecco's Modified Eagle Medium) supplemented with 10% fetal bovine serum (FBS) at 37 C and 5% $CO_2$. After trypsinization and resuspension, the cell suspension is pipetted under sterile conditions on cleanroom cleaned, ultra-thin borosilicate glass slides (25×75 mm, thickness 170 μm), placed inside a 10 cm petri dish, and grown for 2-3 days until they have reached about 80% confluence.

Fixation

The glass slide with the cells grown on top is removed from the petri dish and washed in a glass jar with phosphate buffered saline (PBS) and then submerged in PBS supplemented with 4% paraformaldehyde (PFA) for 30 min.

Permeabilization

The glass slide is washed again with PBS and then submerged in PBS supplemented with 0.25% Triton-X detergent for 15 min. Afterwards, the slide is inserted into a device as described herein for implementing a method of the invention.

Multiplexing Steps

Iterative cycles of sample labeling, imaging and elution are performed in the device and imaging is carried out.

Washing: PBS is applied at a flow rate of 25 μl/s for 10 s. (S0)

Blocking: PBS supplemented with 5% goat serum is applied at a flow rate of 15 μl/s for 10 s and then incubated for 2 min under a continuous flow of 0.015 μl/s. (S2)

Primary antibody binding: PBS supplemented with 5% goat serum and antigen specific mouse anti-human, rabbit anti-human primary antibodies (primary antibodies for any immunohistochemistry and immunofluorescent assay such as described in *Dabbs,* 2014, *supra*) (dilution of 1:10-1:1000, depending on the concentration of the primary antibody solution and the affinity of the antibody) is applied at a flow rate of 15 μl/s for 10 s and then incubated for 15 min under continuous flow of 0.015 μl/s. (S3')

Washing: PBS is applied at a flow rate of 25 μl/s for 10 s. (S3")

Secondary antibody binding: PBS supplemented with 5% goat serum, DAPI and goat anti-rabbit and goat anti-mouse secondary antibodies (dilution of 1:250, 8 μg/ml) labeled with Alexa fluorophores 568 and 647, respectively, is applied at a flow rate of 15 µl/s for 10 s and then incubated for 15 min under continuous flow of 0.015 µl/s. (S3''')

Washing: PBS is applied at a flow rate of 25 µl/s for 10 s. (S3a)

Imaging: Imaging buffer (PBS supplemented with 100 mM of ascorbic acid) is applied at a flow rate of 25 µl/s for 10 s and then continuously applied at 0.015 µl/s throughout the imaging process. (S4)

Images are then acquired on a confocal spinning disk microscope at 40× magnification in three separate channels for the DAPI (4',6-Diamidin-2-phenylindol) stain (exposure at 405 nm) and the two immunofluorescence stains, Alexa fluorophores 488 and 568 (exposure at 488 and 561 nm, respectively). A large area of about 500-1'000 acquisition sites is scanned and 10 focal planes are acquired per channel at each site. The DAPI channel is acquired in each cycle and can thus serve as a reference across cycles for computational alignment of images acquired in different cycles in case of a shift between cycles.

Washing: PBS is applied at a flow rate of 25 µl/s for 10 s.

Elution: Elution buffer (0.1M glycine solution at pH2 supplemented with 0.05% TritonX detergent) is applied at a flow rate of 15 µl/s for 10 s and then incubated for 1 min under a continuous flow of 0.015 µl/s. This step is performed twice.

Example 2: Example of Using an Imaging Buffer of the Invention in a Method of the Invention The present example illustrates the use of an imaging buffer according to the invention used to improve the efficiency of fluorescent molecule removal from samples under high intensity light, which is particularly useful in a method according to the invention.

Formalin fixed HeLa cells were applied to one sample labeling cycle according to the multiplexing protocol as described under Example 1. Then, imaging was performed using either phosphate buffered saline (PBS) alone or in combination with a radical-scavenging agent as imaging buffer. Afterwards, the elution step was performed as described under Example 1 and a second sample labeling cycle was performed, omitting the primary antibody binding step, and a larger imaging area was scanned when compared to the first imaging round, while leaving all other imaging parameters such as laser intensity and exposure time unchanged. In the shown images, the outlined box indicates the acquisition area of the first imaging round.

Figure 3:
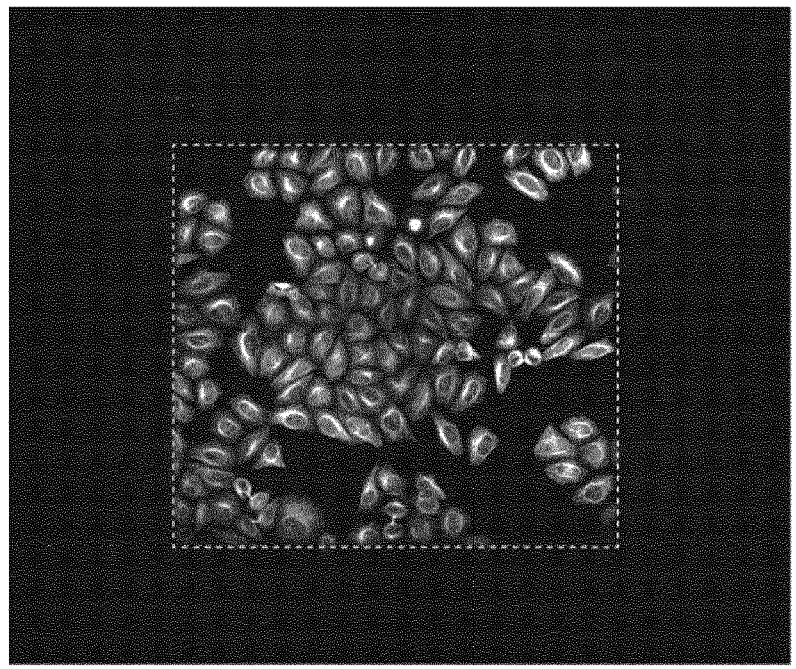
FIG. 3 is an image obtained by confocal fluorescence microscopy at 40× magnification as described in Example 2 of a sample used in a method according to the invention. A: where PBS is used as an imaging buffer according to the multiplexing protocol of the invention and where cross-linking between antigens and antibodies occurs; B: where an imaging buffer consisting of PBS supplemented with a radical scavenger (10 mM Trolox) is used as an imaging buffer according to the multiplexing protocol of the invention and where cross-linking between antigens and antibodies is prevented.
Figure 3:
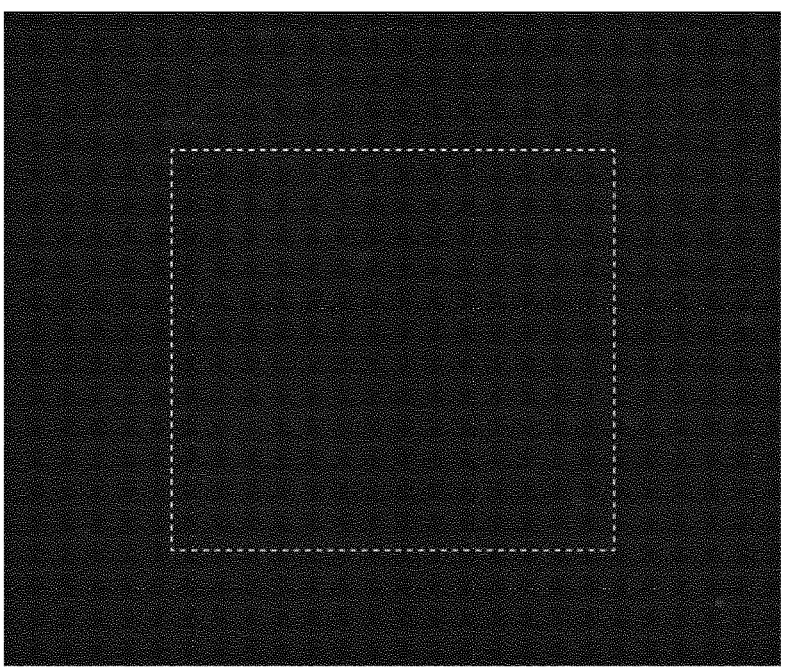

FIG. 3A shows photo-induced cross-linking between antigens and antibodies upon imaging in the presence of PBS alone.

FIG. 3B shows a similar sample exposed to identical pre-labelling and labelling conditions upon imaging in the presence of PBS supplemented with 10 mM Trolox (6-hydroxy-2,5,7,8-tetramethylchroman-2-carboxylic acid).

Those data support that the addition of anti-oxidants and/or radical scavengers to the imaging buffer prevents photo-induced cross-linking between antigens and antibodies used in methods for in situ imaging of samples and thereby increases the efficiency of fluorescent molecule removal from a sample subjected to cycle multiplexing and therefore leads to an increased throughput of a method of the invention.

Figure 4:
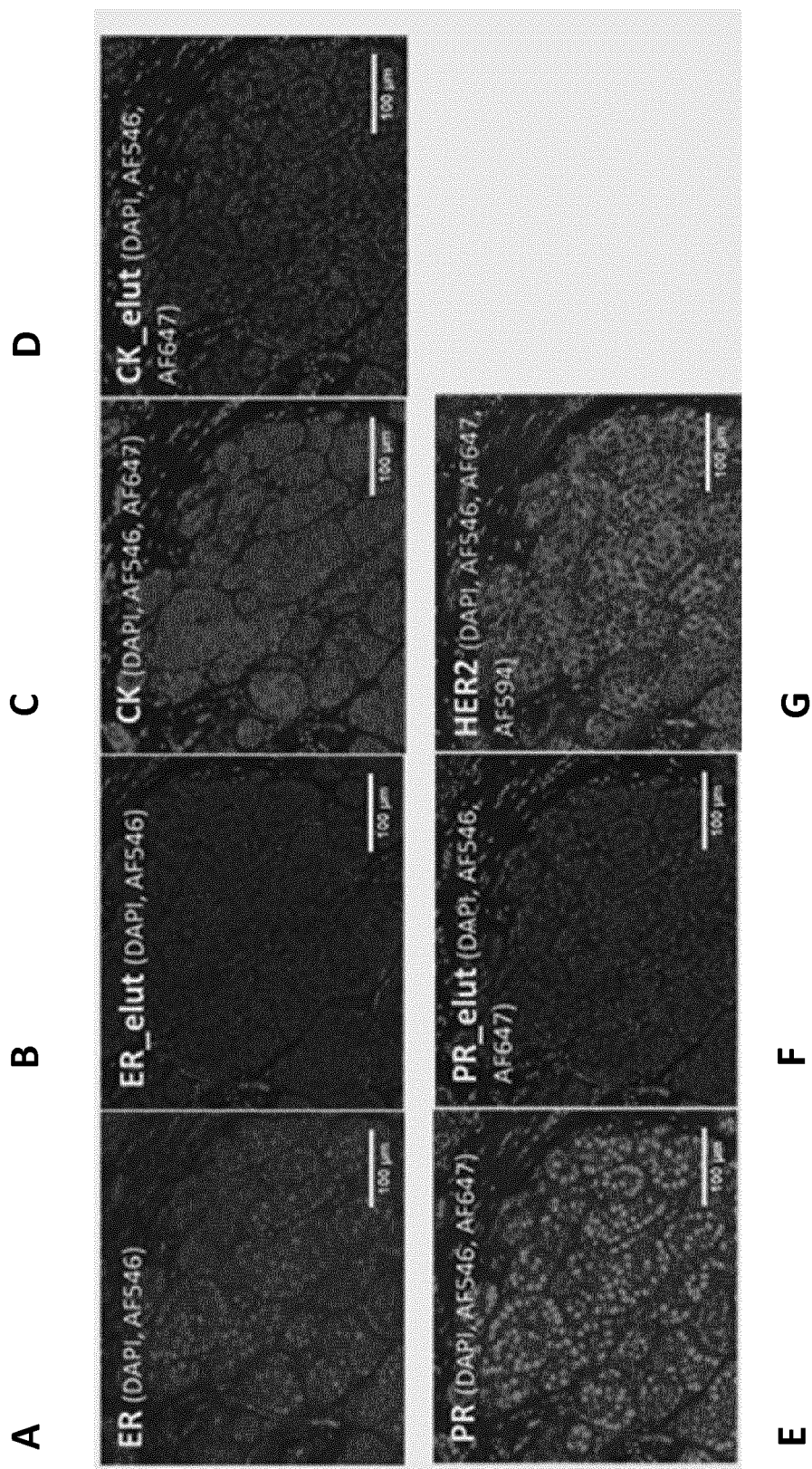
FIG. 4 shows the consecutive images obtained during the multiplexed colocalized staining Example 3 of the various biomarkers on a single breast cancer tissue section. The image order A to G corresponds to the acquisition order indicated in the protocol.

Example 3: Multiplexed Colocalized Staining of ER, CK, PR and HER2 on a Breast Tumor Sample Formalin-fixed paraffin-embedded (FFPE) tissue slides can be stained while also imaging the sample between each step using the methods disclosed in the present invention. As an illustrative example, an FFPE breast tumor section positive to estrogen receptor (ER), progesterone receptor (PR), cytokeratin (CK) and epidermal growth factor receptor 2 (HER2), has been stained using sequential multiplexing according to a method of the invention using in sequence a plurality of reagents and imaging steps determined according to data derived from preliminary test results. The sample has been first prepared for staining through the dewaxing, rehydration and antigen retrieval processes as described in the previous examples and then subjected to a method of in situ imaging of the invention are summarized in Table 2 below. Each marker has been detected in the imaging step using sandwich assays with fluorescent detection probes of different wavelengths (Alexa Fluor). For efficient elution of the antibodies, a combination of elution buffer (EB) and sodium dodecyl sulfate (SDS) has been used in the elution steps. Control images have been taken after each staining (imaging steps 1 to 4), to verify the specific detection of the targeted biomarker (ER, PR, CK, and HER2), and after every elution step from the next cycle, to verify the complete removal of the Abs before staining the next biomarker to be imaged in the next imaging step. In order to image and re-stain the same slide, a glycerol based mounting solution (SlowFade Gold) has been employed. The consecutive images obtained during this method are presented under FIG. 4 and the sample image after each staining (A, C, E and G) and elution step (B, D and F) is shown to demonstrate both the staining and the elution efficiency.

TABLE 2

| | Steps | Reagent | Flow duration (s) | Incubation time (s) | Step time (s) |
|---|---|---|---|---|---|
| Sample preparation | Dewaxing | Histoclear ™ | — | — | 600 |
| | Rehydration | Ethanol from 100% to 0% | — | — | 120 |
| | Antigen retrieval | pH 9 Tris/EDTA | — | — | 2400 |
| Multiplexing (n = 4) | | Cycle 1 | | | |
| | Sample Labelling step 1 | Primary Ab (1) Mouse anti-ER, dil 1/50 | 10 | 240 | 250 |
| | | Washing buffer: PBS | 10 | — | 10 |
| | | Secondary Ab (1) Alexa Fluor 546 goat anti-mouse IgG, dil. 1/40 | 10 | 240 | 250 |
| | | Washing buffer: PBS | 10 | — | 10 |

TABLE 2-continued

| Steps | Reagent | Flow duration (s) | Incubation time (s) | Step time (s) |
|---|---|---|---|---|
| Imaging step 1 | Counterstaining SlowFade Gold + DAPI | — | — | 0 |
| Cycle 2 | | | | |
| Elution step S1' | Elution buffer EB + SDS 0.5% | 10 | 240 | 250 |
| | Washing buffer: PBS | 10 | — | 10 |
| Sample Labelling step 2 | Primary Ab (2) Mouse anti-CK, dil 1/100 | 10 | 120 | 130 |
| | Washing buffer: PBS | 10 | — | 10 |
| | Secondary Ab (2) Alexa Fluor 647 goat anti-mouse IgG, dil. 1/40 | 10 | 120 | 130 |
| | Washing buffer: PBS | 10 | — | 10 |
| Imaging step 2 | = identical as Imaging step 1 | | | |
| Cycle 3 | | | | |
| Elution step S1'' | = idem as S1' | | | |
| Sample Labelling step 3 | Primary Ab (3) Mouse anti-PR, d il 1/100 | 10 | 240 | 250 |
| | Washing buffer: PBS | 10 | — | 10 |
| | Secondary Ab (3) Alexa Fluor 647 goat anti-mouse IgG, dil. 1/40 | 10 | 240 | 250 |
| | Washing buffer: PBS | 10 | — | 10 |
| Imaging step 3 | = identical as Imaging step 1 | | | |
| Cycle 4 | | | | |
| Elution step S1''' | = identical as S1' | | | |
| Sample Labelling step 4 | Primary Ab (4) Rabbit anti-HER2, dil 1/250 | 10 | 120 | 130 |
| | Washing buffer: PBS | 10 | — | 10 |
| | Secondary Ab (4) Alexa Fluor 594 goat anti-mouse IgG, dil. 1/40 | 10 | 120 | 130 |
| | Washing buffer: PBS | 10 | — | 10 |
| Imaging step 4 | = identical as Imaging step 1 | | | |
| Total Multiplexing | | 220 | 2160 | 2380 |

The results show that a multiplexing method according to the invention advantageously allows the obtaining of multiplexed colocalized stainings for various biomarkers on the same biological sample with high staining efficiency and contrasts, wherein the staining is selectively carried out on the biomarkers of interest without interaction between the different imaging reagents for the various biomarkers and in limited total experimentation time of about 40 minutes.

The invention claimed is:

1. A method for in situ imaging of samples by cycle multiplexing comprising the steps of:
   (i) providing a sample immobilized on a sample support;
   (ii) providing a microfluidic device comprising a microfluidic chamber, at least one fluid inlet at one end of said microfluidic chamber and at least one fluid outlet at another end of said microfluidic chamber configured to conduct a fluid supplied from a fluid feeding system under pressure through the microfluidic chamber for advective transport of fluidic substances and reagents inside said microfluidic chamber in a uniform manner, wherein at least one wall of the microfluidic chamber is formed by the sample support and wherein the volume of the microfluidic chamber is from about 2.5 and 200 µl;
   (iii) mounting said sample support over said microfluidic chamber with the sample facing the inside of the microfluidic chamber;
   (iv) injecting in sequence a plurality of reagents, including at least one imaging probe, through the fluid inlet into the microfluidic chamber, at a flow rate in a range between about 1 µl/s and about 100 µl/s;
   (v) imaging a signal emitted by components of the sample reacted with said at least one imaging probe;
   (vi) repeating steps (iv) and (v) with different imaging probes;
   wherein said injecting in sequence a plurality of reagents includes:
      an elution step where an elution buffer is injected for removing undesirable material potentially remaining on the sample;
      a non-specific binding blocking step where a blocking buffer is injected;
      a sample labelling step where an imaging probe is injected; and
      an optional pre-imaging step where an imaging buffer is injected, wherein each of these steps may be preceded and/or followed by an optional washing step wherein a washing buffer is injected,
   wherein said at least one imaging probe results from the injection of a sequence of specific antibodies as labelling probes and chromogen or fluorescent detection molecules, targeting the molecular entities to be analyzed within the said sample.

2. The method according to claim 1, wherein each step in the sequence of injected plurality of reagents comprises for each reagent two flow rate steps:
   a first flow rate step where the reagent is injected at an initial flow rate in a range between about 1 μl/s and about 100 μl/s;
   a second flow rate step where the same reagent is injected at a lower flow (typically from about 0.001 to about 1.0 μl/s) to ensure incubating said reagent with the sample, before injecting the next reagent in the sequence.

3. The method according to claim 2, wherein the first flow rate step lasts from about 1 s to about 120 s.

4. The method according to claim 2, wherein the second flow rate step of a reagent lasts from about 1 min to about 30 min.

5. The method according to claim 1, wherein the sample labelling step comprises a first step wherein a primary antibody is injected (S3'), a washing step wherein a washing buffer is injected (S3") and a further step wherein a secondary antibody is injected (S3"').

6. The method according to claim 1, wherein the step of injecting in sequence a plurality of reagents includes:
   a washing step wherein a washing buffer is injected (S0);
   a non-specific binding blocking step (S2) where a blocking buffer is injected;
   a sample labelling step where an imaging probe is injected (S3);
   a washing step wherein a washing buffer is injected (S3a);
   an optional pre-imaging step (S4) where an imaging buffer is injected, wherein the sample labelling step comprises a first step wherein a primary antibody is injected (S3'), a washing step wherein a washing buffer is injected (S3") and a further step wherein a secondary antibody is injected (S3"').

7. The method according to claim 1, the sample labeling step comprises injecting at least one labeled RNA or DNA probe for in-situ hybridization with DNA/RNA material within the sample.

8. The method according to claim 7, wherein the sample labeling step further comprises applying temperature cycles within the microfluidic chamber for hybridizing DNA/RNA material within the sample with said at least one labeled RNA or DNA probe.

9. The method according to claim 7, wherein under step (vi) the elution step is carried out while applying a temperature cycle for ensuring removal of undesirable in-situ hybridized probes or markers potentially remaining on the sample before repeating the method with another sample labelling step.

10. The method according to claim 1, wherein the imaging step (v) is conducted by fluorescence microscopy or bright field microscopy.

11. The method according to claim 1, wherein the method comprises at least about 2 to 80 cycles of steps (iv) to (v).

12. The method according to claim 1, wherein the said pre-imaging step is present.

* * * * *

UNITED STATES PATENT AND TRADEMARK OFFICE
CERTIFICATE OF CORRECTION

PATENT NO. : 10,634,671 B2
APPLICATION NO. : 16/076000
DATED : April 28, 2020
INVENTOR(S) : Ata Tuna Ciftlik et al.

Page 1 of 1

It is certified that error appears in the above-identified patent and that said Letters Patent is hereby corrected as shown below:

In the Specification

Column 6,
Line 60, "where a imaging an imaging probe" should read --where an imaging probe--.

In the Claims

Column 17,
Line 8, "1 μVs" should read --1 μl/s--.
Line 23, "(S3")." should read --(S3"").--.

Signed and Sealed this
First Day of September, 2020

Andrei Iancu
*Director of the United States Patent and Trademark Office*